(12) United States Patent
Ogawa et al.

(10) Patent No.: US 9,039,664 B2
(45) Date of Patent: May 26, 2015

(54) ELASTIC SEAL MEMBER FOR PREFILLED SYRINGE

(75) Inventors: Yukihiro Ogawa, Ibaraki (JP); Yasuyuki Shiraishi, Ibaraki (JP); Taiji Horita, Ibaraki (JP); Ichiro Suzuki, Nagoya (JP)

(73) Assignee: Taisei Kako Co., Ltd. (JP)

( * ) Notice: Subject to any disclaimer, the term of this patent is extended or adjusted under 35 U.S.C. 154(b) by 0 days.

(21) Appl. No.: 14/112,092

(22) PCT Filed: Apr. 16, 2012

(86) PCT No.: PCT/JP2012/060217
§ 371 (c)(1),
(2), (4) Date: Nov. 13, 2013

(87) PCT Pub. No.: WO2012/147545
PCT Pub. Date: Nov. 1, 2012

(65) Prior Publication Data
US 2014/0066859 A1    Mar. 6, 2014

(30) Foreign Application Priority Data

Apr. 26, 2011 (JP) ................................. 2011-097835

(51) Int. Cl.
*A61M 5/24* (2006.01)
*A61M 5/315* (2006.01)
*B01L 3/00* (2006.01)

(52) U.S. Cl.
CPC ......... *A61M 5/2466* (2013.01); *A61M 5/31513* (2013.01); *A61M 5/31511* (2013.01); *A61M 5/315* (2013.01); *B01L 3/50825* (2013.01)

(58) Field of Classification Search
CPC ... A61M 5/24; A61M 5/2429; A61M 5/2455; A61M 5/2466; A61M 2/283; A61M 5/315; A61M 5/31511; A61M 5/31513; A61M 2005/247; B01L 3/50825
USPC ......... 604/181, 187, 200, 201, 202, 203, 204, 604/205, 206, 218, 230, 231
See application file for complete search history.

(56) References Cited

U.S. PATENT DOCUMENTS

| | | | | |
|---|---|---|---|---|
| 4,997,423 | A | * | 3/1991 | Okuda et al. .................. 604/230 |
| 6,007,520 | A | * | 12/1999 | Sudo ............................. 604/181 |
| 6,280,431 | B1 | * | 8/2001 | Domkowski et al. ......... 604/411 |
| 2005/0113747 | A1 | * | 5/2005 | Moir ............................... 604/87 |

FOREIGN PATENT DOCUMENTS

| | | |
|---|---|---|
| JP | 7-323072 | 12/1995 |
| JP | 08506749 A | 7/1996 |

(Continued)

*Primary Examiner* — Bhisma Mehta
*Assistant Examiner* — Nicholas Meghri
(74) *Attorney, Agent, or Firm* — Wood, Phillips, Katz, Clark & Mortimer

(57) ABSTRACT

In a prefilled syringe including an elastic seal member to be pierced with a needle for use to eject a protein pharmaceutical preparation therefrom, the elastic seal member ensures smooth and reliable piercing thereof with the needle while reliably preventing an active substance of the protein pharmaceutical preparation from being adsorbed thereon. When a protective film (3) is laminated to a top surface of a seal body (2) of an elastic material, the protective film (3) is stretched to a greater extent by a recess (4) provided in the top surface. Further, the piercing portion to be pierced with the needle is provided in a bottom of the recess (4). Thus, the protective film (3) is formed as locally having a smaller thickness in the piercing portion.

5 Claims, 5 Drawing Sheets

(56) References Cited

FOREIGN PATENT DOCUMENTS

| JP | 11511358 A | 10/1999 |
| JP | 2001-190667 A | 7/2001 |
| JP | 20022506695 A | 3/2002 |
| JP | 2002-172166 A | 6/2002 |

\* cited by examiner

ELASTIC SEAL MEMBER FOR PREFILLED SYRINGE

TECHNICAL FIELD

The present invention relates to a prefilled-syringe elastic seal member to be used as a syringe gasket or a plug for a prefilled syringe.

BACKGROUND ART

As disclosed in PTL1 to PTL4, various types of prefilled syringes are conventionally known. A known gasket for a prefilled syringe is described in PTL5.

CITATION LIST

Patent Literature

PTL1: JP-HEI11(1999)-511358A
PTL2: JP-2002-506695A
PTL3: JP-HEI8(1996)-506749A
PTL4: JP-2002-172166A
PTL5: JP-2001-190667A

The prior-art prefilled syringes disclosed in PTL1 to PTL4 mainly include a glass syringe cylinder and a syringe gasket (elastic seal member) of a butyl rubber. A space defined by the gasket and the syringe cylinder serves as a drug containing portion. The prefilled syringes are distributed in the market with the drug containing portion thereof aseptically filled with a content liquid. The prefilled syringes include a needle through which the content liquid is ejected from the drug containing portion. The prefilled syringes are constructed such that the content liquid is ejected from the drug containing portion with a center piercing portion of the gasket pierced with the needle.

The prior-art gasket described in PTL5 is such that a gasket surface is laminated (formed) with a film of a fluorine-containing resin, an ultra-high molecular weight polyethylene resin or a polypropylene resin to be thereby improved in chemical resistance, i.e., resistance to a chemical liquid.

SUMMARY OF INVENTION

Technical Problem

In recent years, research and development have been rapidly conducted on biomedicines, and there has been a demand for using the prefilled syringes for the biomedicines. Since such a biomedicine is a type of protein pharmaceutical preparation, the butyl rubber gasket is liable to adsorb proteins contained in the biomedicine to thereby reduce the efficacy of the biomedicine during storage. On the other hand, biomedicine packages other than the prefilled syringes are laminated with a film of a polytetrafluoroethylene or an ultra-high molecular weight polyethylene to prevent the adsorption of the proteins on the packages. The inventors of the present invention produced gaskets laminated with the same film for the prefilled syringes, and conducted various tests on the film-laminated gaskets. As a result, problems such as breakage and flexure of the needle and separation of the film occurred due to higher hardness of the film. Further, the inventors produced trial products of gaskets laminated with a thinner film for easier piercing with the needle. In this case, problematically, the film was broken or holed in the film laminating step, because the film is too thin.

It is therefore an object of the present invention to provide a gasket (elastic seal member) to be pierced with a needle to eject a content liquid through the needle for use in a prefilled syringe, the elastic seal member ensuring smooth and reliable piercing of the gasket with the needle while reliably preventing an active substance of the content liquid from being adsorbed on the gasket.

Solution to Problem

To attain the above object, the present invention takes the following technical measures.

The present invention provides an elastic seal member for a prefilled syringe including a drug containing portion filled with a content liquid, the elastic seal member being adapted to seal the drug containing portion and having a piercing portion to be pierced with a needle for use, the elastic seal member comprising a seal body of an elastic material and a protective film laminated to at least a surface portion of the body opposed to the drug containing portion, wherein the protective film locally has a smaller thickness in the piercing portion than around the piercing portion.

In the inventive elastic seal member for the prefilled syringe, the protective film locally has a smaller thickness in the piercing portion, so that a tip of the needle can easily penetrate through the protective film when the piercing portion is pierced with the needle. This prevents the protective film from being separated from the seal body. Further, the protective film can have a necessary and sufficient thickness around the piercing portion. Therefore, the film is free from breakage and holes in the film laminating step, thereby reliably preventing an active substance of the content liquid from being adsorbed on the seal body.

The present invention further provides an elastic seal member for a prefilled syringe including a drug containing portion filled with a content liquid, the elastic seal member being adapted to seal the drug containing portion and having a piercing portion to be pierced with a needle for use, the elastic seal member comprising a seal body of an elastic material and a protective film laminated to at least a surface portion of the body opposed to the drug containing portion, wherein the body preferably has a recess provided in the surface portion thereof for stretching the film to a greater extent when the film is laminated to the body, wherein the piercing portion is provided in a bottom of the recess, wherein the protective film is formed as locally having a smaller thickness in the piercing portion than around the piercing portion by stretching the protective film in intimate contact with a part of the surface portion present in the recess. With the piercing portion thus provided in the bottom of the recess, a portion of the film present in the piercing portion is stretched to a greater extent as having a smaller thickness when the film is laminated to the body. This makes it possible to improve the productivity and stabilize the quality of the product.

More preferably, the surface portion of the seal body opposed to the drug containing portion is substantially conformal to a bottom surface of the syringe, and the recess is provided at the center of the surface portion so that a tip of the needle penetrating through the piercing portion is accommodated in the recess. With this arrangement, a top surface of the seal body (the surface portion of the seal body opposed to the drug containing portion) has substantially the same shape as the bottom surface of the syringe. Therefore, the seal body can be slid to bring the top surface thereof into abutment against the bottom surface of the syringe, making it possible to minimize the amount of the content liquid remaining in the drug containing portion. Thus, the amount of an expensive protein pharmaceutical preparation left unused in the drug containing portion can be minimized. Further, the tip of the needle can be accommodated in the recess utilized for forming the smaller thickness portion of the protective film to be thereby prevented from abutting against the bottom surface of the syringe. This makes it possible to prevent the breakage of the needle and the syringe.

In the present invention, the content liquid is preferably a protein pharmaceutical preparation, and the protective film is preferably a film of a fluorine-containing resin or an ultra-high molecular weight polyethylene predisposed to prevent a protein from adsorbing onto the film.

Further, a surface adhesion force between the protective film and the seal member in the piercing portion is preferably greater than an external force which acts on the protective film to separate the protective film from the seal body when the piercing portion is pierced with the needle.

The portion of the protective film present in the piercing portion preferably has a minimum thickness that is 30 to 50% of an average thickness of a portion of the protective film outside the piercing portion. More specifically, the protective film preferably has a thickness of about 30 to about 50 μm in the piercing portion, and has an average thickness of about 100 μm outside the piercing portion.

Advantageous Effects of Invention

In the prefilled syringe adapted to eject the content liquid therefrom with the elastic seal member pierced with the needle for use, according to the present invention, it is possible to ensure smooth and reliable piercing of the gasket with the needle while reliably preventing the active substance of the content liquid from being adsorbed on the gasket.

DESCRIPTION OF EMBODIMENTS

Preferred embodiments of the present invention will hereinafter be described with reference to the drawings.

Figure 1:
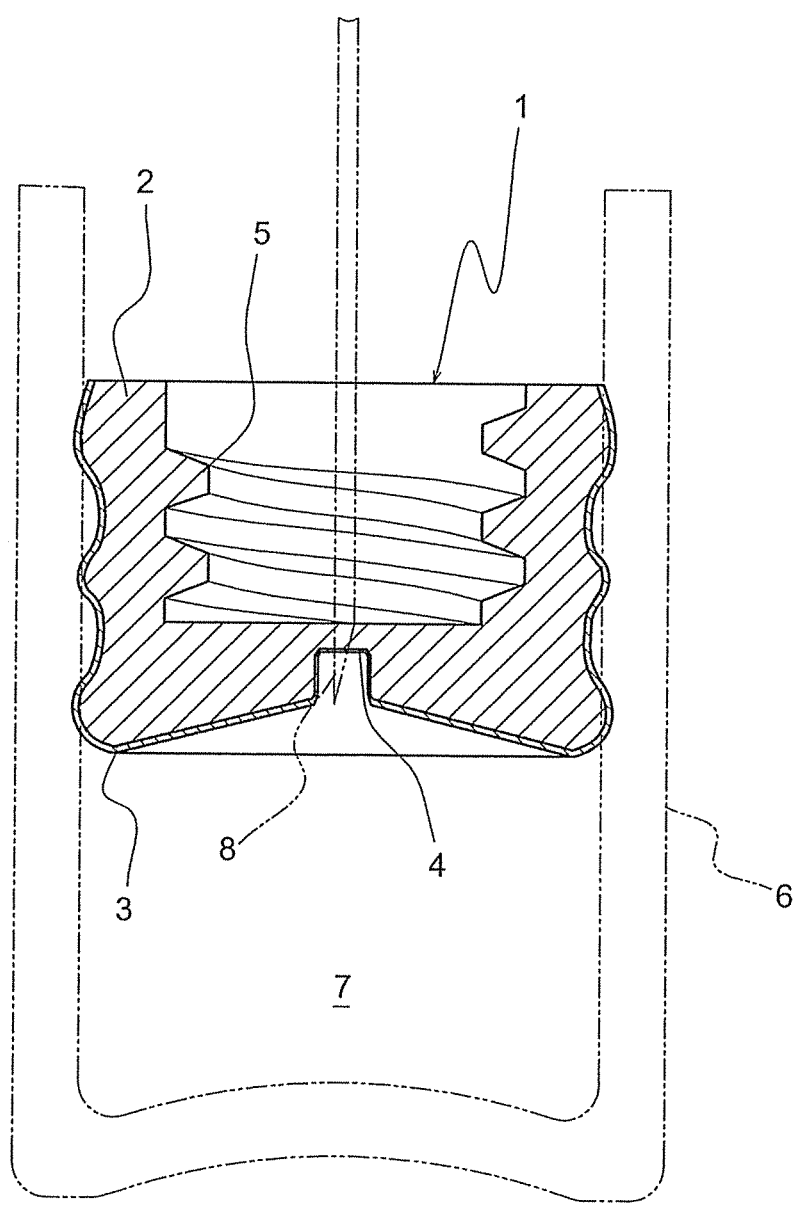
FIG. 1 is a sectional view of a prefilled syringe elastic seal member according to a first embodiment of the present invention.

FIG. 1 illustrates an elastic seal member 1 for a prefilled syringe according to a first embodiment of the present invention. The seal member 1 is fitted in a bottomed cylindrical syringe 6 having an inside space serving as a drug containing portion 7 for containing a protein pharmaceutical preparation (content liquid), thereby sealing the drug containing portion 7 filled with the protein pharmaceutical preparation. This prefilled syringe includes a needle 8 for ejecting the protein pharmaceutical preparation from the drug containing portion 7. The needle 8 penetrates through a center piercing portion of the seal member 1 from a back side (an upper side in FIG. 1) to a front side (a lower side in FIG. 1) of the seal member 1. In this state, the seal member 1 is slid downward with respect to the syringe 6 to pressurize the protein pharmaceutical preparation, whereby the protein pharmaceutical preparation is ejected from a tip of the needle 8 through the needle 8. A proper mechanism may be provided for operating the seal member 1 and the needle 8. The seal member 1 has a threaded fixture portion 5 provided on the back side thereof for attaching a plunger or the like to the seal member.

The elastic seal member 1 includes a seal body 2 of an elastic material, and a protective film 3 laminated to a front surface of the seal body 2 opposed to the drug containing portion and an outer peripheral surface of the seal body 2. The seal body 2 may be produced by vulcanizing a proper unvulcanized rubber such as a butyl rubber, a natural rubber, a polyisoprene, a polybutadiene, a styrene-butadiene rubber or an ethylene-propylene rubber in a molding die, or by molding an elastic material through any other molding method such as an injection molding method.

The seal body 2 has a round recess 4 provided at the center of the front surface thereof so that the protective film 3 can be locally stretched to a greater extend when being laminated to the seal body 2. A bottom of the recess 4 serves as the piercing portion to be pierced with the needle. The front surface (so-called top surface) of the seal body 2 to be opposed to the drug containing portion 7 is substantially conformal to a bottom surface of the syringe 6, so that a minimum amount of the protein pharmaceutical preparation remains in the drug containing portion 7 with the elastic seal member 1 in abutment against the bottom surface of the syringe 6. When the protein pharmaceutical preparation is ejected, the tip of the needle 8 is accommodated in the recess 4. In this state, the needle 8 and the elastic seal member 1 are unitarily axially moved with respect to the syringe 6.

The protective film 3 is preferably made of a fluorine-containing resin such as a polytetrafluoroethylene or an ethylene-tetrafluoroethylene copolymer, or an ultra-high molecular weight polyethylene resin. A proper laminating method may be employed for laminating the protective film 3 to the seal body 2. In this embodiment, the protective film 3 has a relaxed state wherein the protective film 3 has a first thickness. The protective film 3 has an applied state wherein it is formed as locally having a smaller thickness in the piercing portion than around the piercing portion by locally stretching the protective film 3 in intimate contact with the surface of the seal body 2 in the recess 4.

Figure 2:
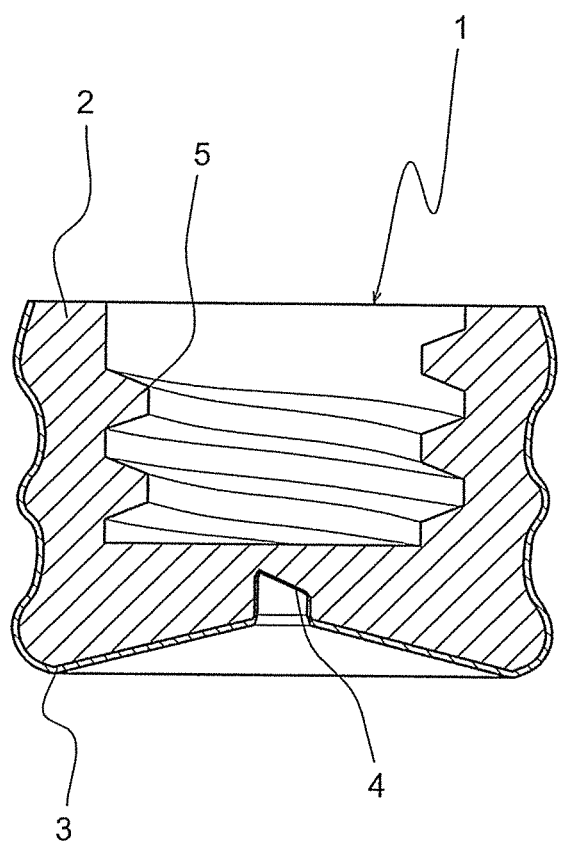
FIG. 2 is a sectional view of a prefilled syringe elastic seal member according to a second embodiment of the present invention.

The recess 4 may have any proper structure as long as the protective film 3 can be formed as locally having a smaller thickness. The recess 4 may have a flat bottom surface as shown in FIG. 1, or may have a tapered bottom surface as shown in FIG. 2. The recess 4 may have a smoothly rounded shape as shown in FIG. 3.

Figure 4:
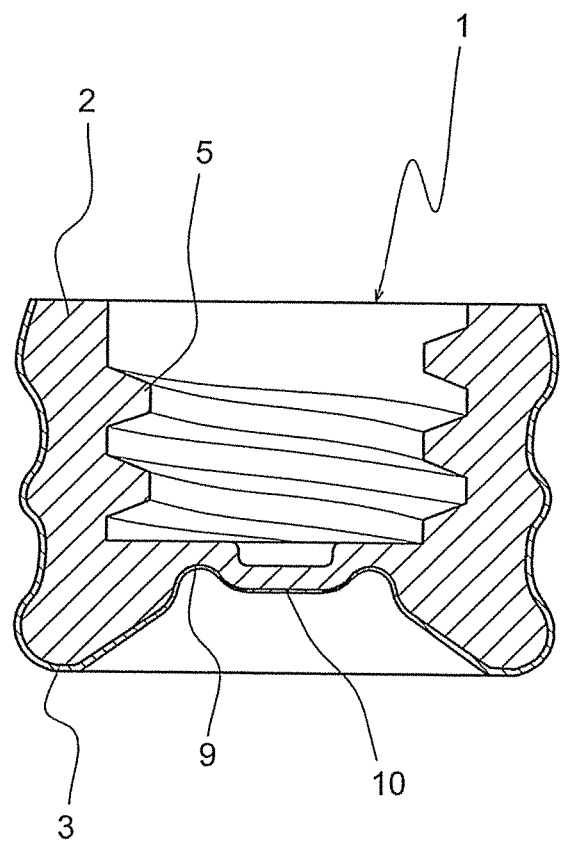
FIG. 4 is a sectional view of a prefilled syringe elastic seal member according to a fourth embodiment of the present invention.

FIG. 4 shows another embodiment in which, rather than locally providing the recess at the center, the entire top surface of the seal body 2 is indented in a crater shape and a trapezoidal protuberance 10 is provided in a center portion of the indentation. With this arrangement, the protective film 3 is significantly stretched by the center portion of the top surface in the presence of the protuberance 10 when the seal body 2 is laminated with the protective film 3. Thus, a center portion of the protective film 3 present in the piercing portion can be thinned to about half the thickness of a portion of the protective film 3 present on the outer peripheral portion of the seal body 2.

Figure 3:
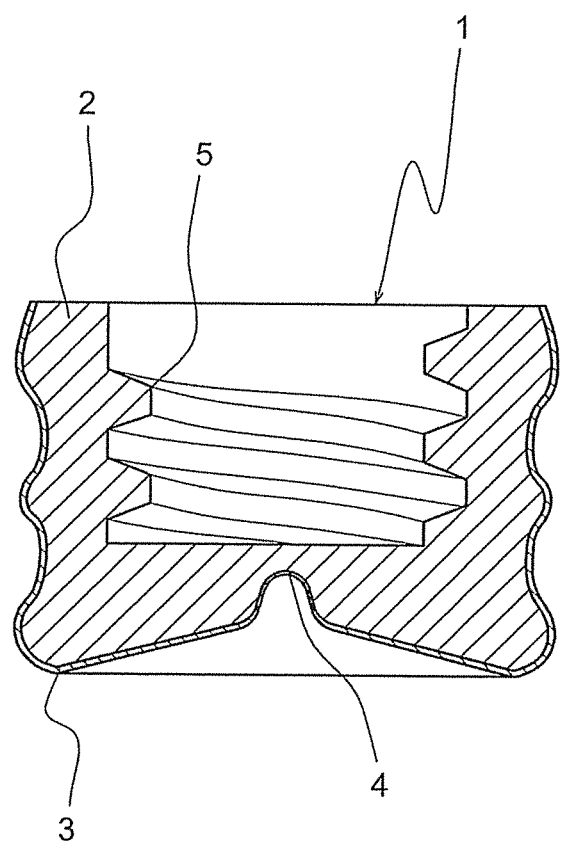
FIG. 3 is a sectional view of a prefilled syringe elastic seal member according to a third embodiment of the present invention.
Figure 5:
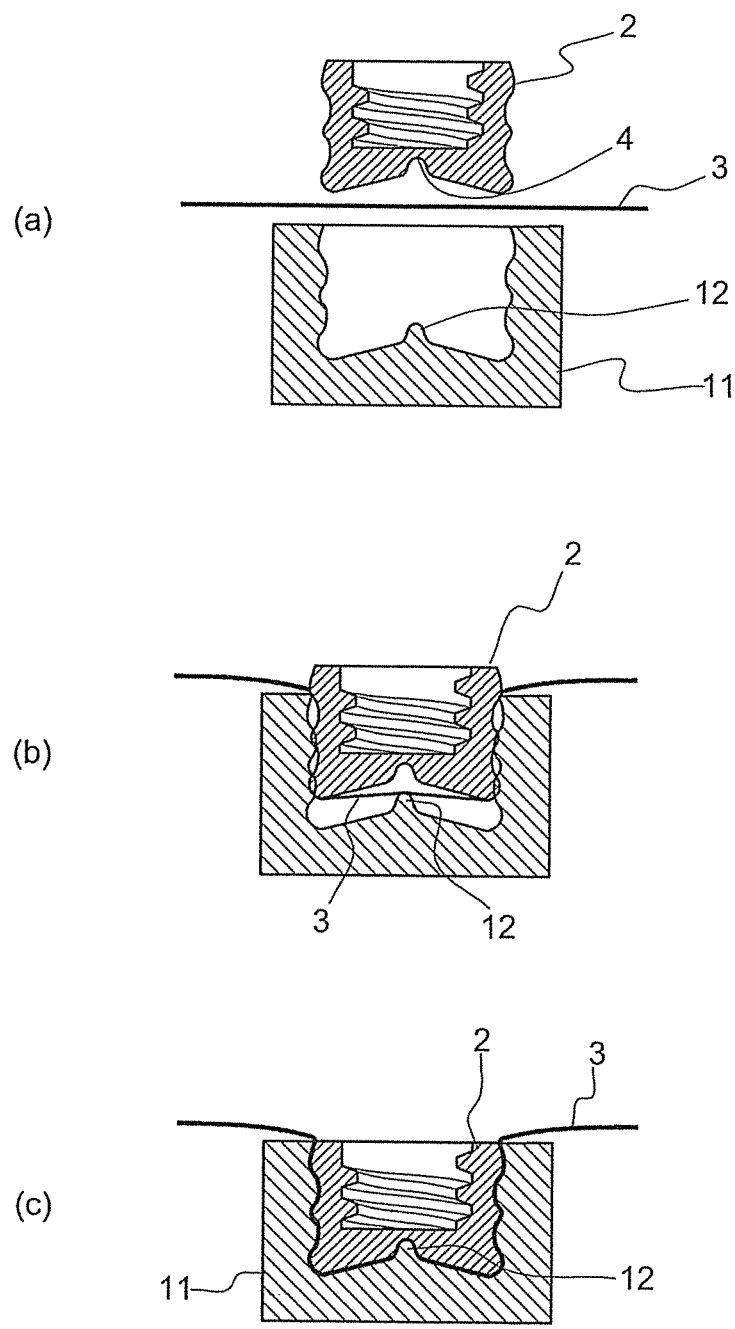
FIG. 5 are process diagrams showing a laminating step of laminating a protective film for the elastic seal member shown in FIG. 3.

FIG. 5 are process diagrams showing a laminating step of laminating the protective film 3 for the elastic seal member 1 shown in FIG. 3. As shown in FIGS. 5(a) and 5(b), a seal body 2 preliminarily molded and vulcanized and a protective film 3 heated to be temperature-controlled are stacked together and inserted into a molding die 11. The protective film 3 is first held between a peripheral portion of the top surface of the seal body 2 and the molding die 11, and a portion of the protective film 3 opposed to the top surface is stretched in spaced relation to the top surface. The molding die 11 has a projection 12 provided in a bottom center portion thereof and complementary in shape to the recess 4. The projection 12 is brought into abutment against the center portion of the stretched protective film 3, so that the portion of the protective film 3 opposed to the recess 4 is locally significantly stretched to be thereby thinned. Then, as shown in FIG. 5(*c*), the seal body 2 is completely squeezed into the molding die 11. Thus, the protective film 3 is pressed against at least the top surface of the seal body 2 to be thereby reliably brought into intimate contact with at least the top surface of the seal body 2 by heat applied from the molding die 11. A surface adhesion force between the protective film 3 and the seal body 2 in the piercing portion is preferably greater than an external force which acts on the protective film 3 to separate the protective film 3 from the seal body 2 when the piercing portion is pierced with the needle 8.

The protective film 3 is not necessarily required to be pressed against the outer peripheral portion of the seal body 2 by the molding die, but may be brought into intimate contact with the seal body 2 by a shrinking process.

The present invention is not limited to the embodiments described above, but design modifications may be made to the embodiments. In the embodiments described above, the protective film 3 is laminated to the preliminarily molded and vulcanized seal body by way of example, but may be laminated to the seal body when an unvulcanized rubber is molded and vulcanized into the seal body. Further, the seal body may be prepared by an injection molding process.

REFERENCE SIGNS LIST

1: ELASTIC SEAL MEMBER
2: SEAL BODY
3: PROTECTIVE FILM
4: RECESS
5: THREADED FIXTURE PORTION
6: SYRINGE
7: DRUG CONTAINING PORTION
8: NEEDLE

The invention claimed is:

1. An elastic seal member for a prefilled syringe including a drug containing portion filled with a content liquid, the elastic seal member being adapted to seal the drug containing portion and having a piercing portion to be pierced with a needle for use, the elastic seal member comprising:
   a seal body of an elastic material; and
   a protective film laminated to at least a surface portion of the seal body opposed to the drug containing portion,
   wherein the protective film has a relaxed state wherein the protective film has a first thickness,
   wherein the protective film has an applied state with the protective film laminated to the surface portion of the seal body,
   wherein in the applied state, the protective film is changed from the relaxed state by being locally stretched more in the piercing portion than around the piercing portion as a result of which the laminated protective film is locally changed from the first thickness and has a locally smaller thickness in the piercing portion than around the piercing portion.

2. The prefilled-syringe elastic seal member according to claim 1,
   wherein the seal body has a recess provided in the surface portion thereof,
   wherein the piercing portion is provided in a bottom of the recess,
   wherein the protective film is in intimate contact with a part of the surface portion present in the recess.

3. The prefilled-syringe elastic seal member according to claim 2,
   wherein the surface portion of the seal body opposed to the drug containing portion is substantially conformal to a bottom surface of the syringe,
   wherein the recess is provided at a center of the surface portion so that a tip of the needle penetrating through the piercing portion is accommodated in the recess.

4. The prefilled-syringe elastic seal member according to claim 1,
   wherein the content liquid is a protein pharmaceutical preparation,
   wherein the protective film is a film of a fluorine-containing resin or an ultra-high molecular weight polyethylene predisposed to prevent a protein from adsorbing onto the film.

5. The prefilled-syringe elastic seal member according to claim 1, wherein a surface adhesion force between the protective film and the seal member in the piercing portion is greater than an external force which acts on the protective film to separate the protective film from the seal body when the piercing portion is pierced with the needle.

\* \* \* \* \*